US006621567B1

(12) United States Patent
Haga et al.

(10) Patent No.: US 6,621,567 B1
(45) Date of Patent: Sep. 16, 2003

(54) SURFACE INSPECTING METHOD AND SURFACE INSPECTING DEVICE

(75) Inventors: Kazumi Haga, Tokyo (JP); Motoshi Sakai, Tokyo (JP); Zenta Ushiyama, Tokyo (JP)

(73) Assignee: NewCreation Co., Ltd., Tokyo (JP)

( * ) Notice: Subject to any disclaimer, the term of this patent is extended or adjusted under 35 U.S.C. 154(b) by 0 days.

(21) Appl. No.: 09/462,168

(22) PCT Filed: Jun. 18, 1998

(86) PCT No.: PCT/JP98/02693

§ 371 (c)(1),
(2), (4) Date: Mar. 24, 2000

(87) PCT Pub. No.: WO99/01751

PCT Pub. Date: Jan. 14, 1999

(30) Foreign Application Priority Data

Jul. 1, 1997 (JP) ............................................. 9-175999

(51) Int. Cl.$^7$ ............................................. G01N 21/88
(52) U.S. Cl. ............................... 356/237.2; 356/237.3; 356/237.5
(58) Field of Search .......................... 356/237.2, 237.3, 356/237.4, 237.5; 250/559.45; 382/143, 144, 149

(56) References Cited

U.S. PATENT DOCUMENTS

| 5,251,010 A | * | 10/1993 | Maltby, Jr. ................... 356/613 |
| 5,583,632 A | * | 12/1996 | Haga ............................ 356/129 |
| 5,748,305 A | * | 5/1998 | Shimono et al. .......... 356/237.2 |

FOREIGN PATENT DOCUMENTS

| JP | 7-209201 | 1/1994 |
| JP | 7-209202 | 1/1994 |
| JP | 7-325036 | 5/1994 |
| JP | 8-292021 | 4/1995 |
| JP | 9-148411 | 11/1995 |

OTHER PUBLICATIONS

Patent Abstracts of Japan, JP, 9–148411, A (Yokogawa Precision K.K., et al), Jun. 6, 1997.
Patent Abstracts of Japan, JP, 7–209202, A (Canon Inc.), Aug. 11, 1995.
Patent Abstracts of Japan, JP, 7–209201, A (Canon Inc.), Aug. 11, 1995.
Patent Abstracts of Japan, JP, 8,292021, A (Matsushita Electric Ind. Co., Ltd., Nov. 5, 1996.
Patent Abstracts of Japan, JP, 7–325036, A (New Kurieishiyon: K.K.), Dec. 12, 1995.

* cited by examiner

*Primary Examiner*—Zandra V. Smith
(74) *Attorney, Agent, or Firm*—Crowell & Moring LLP

(57) ABSTRACT

A surface examining method and a surface examining apparatus, in which a large-sized lens of an object-side telecentric optical system is not required and which can observe a surface to be examined in a wide region. A surface examining method for examining a surface of an object to be measured, by observing a light reflected from the object through an object-side telecentric optical system or an image-object-side telecentric optical system, comprises the steps of; arranging the object-side telecentric optical system or the image-object-side telecentric optical system so that an optical axis thereof is inclined with respect to a direction normal to the object to be measured, and observing the light reflected from the object to be measured.

4 Claims, 3 Drawing Sheets

SURFACE INSPECTING METHOD AND SURFACE INSPECTING DEVICE

TECHNICAL FIELD

The present invention relates to a surface examining (or inspection) method and a surface examining (or inspection) apparatus, for examining or inspecting a state of a surface of an object to be measured, for example, a surface of a semiconductor wafer or the like.

BACKGROUND OF THE INVENTION

As a conventional surface examining apparatus, for example, the apparatus disclosed in the Japanese Patent Application No. Tokugan-Hei 6-141118, or the like is known. In such a surface examining apparatus, an object to be measured is illuminated with a parallel light from an illuminating optical system, and then the state of a surface thereof is observed by passing the reflected light from the surface through an object-side telecentric optical system.

An object-side telecentric optical system has an advantage of setting the distance (distance to object) between a lens of an object-side telecentric optical system and a surface to be examined, of an object to be measured desirably. Therefore, in such a surface examining apparatus, an object-side telecentric optical system can be arranged more freely.

However, in such a surface examining apparatus, because a normal line of a surface to be examined coincides with an optical axis of an object-side telecentric optical system, there is a problem that a large-sized lens of an object-side telecentric optical system is required in order to observe the surface to be examined in a wide region. Further, there is another problem that the size of the surface examining apparatus is large in a direction normal to the surface to be examined. Such problems also occur in the case of using an image-object-side telecentric optical system instead of an object-side telecentric optical system.

DISCLOSURE OF THE INVENTION

The present invention was developed in view of the above-described problems. The present invention was completed on the basis of inventors' study about a surface examining method and a surface examining apparatus, in which a large-sized lens of an object-side telecentric optical system is not required and which enables observation in a wide region on the surface to be examined.

That is, in accordance with one aspect of the present invention, the surface examining method for examining a surface of an object to be measured, by observing a light reflected from the object through an object-side telecentric optical system or an image-object-side telecentric optical system, comprises the steps of; arranging the object-side telecentric optical system or the image-object-side telecentric optical system so that an optical axis thereof is inclined with respect to a direction normal to the object to be measured, and observing the light reflected from the object to be measured.

In such a surface examining method, because the object-side telecentric optical system or the image-object-side telecentric optical system is arranged so that an optical axis thereof is inclined with respect to a direction normal to the object to be measured, it is possible to examine a wide region on the surface to be examined and to reduce the size of the apparatus for examining, in a direction normal to the surface to be examined.

In the surface examining method, it is preferable that the surface examining method further comprises the step of forming an image of the light issued from the object-side telecentric optical system or the image-object-side telecentric optical system at an image pickup part, wherein the image pickup part is inclined so as to coincide with an image plane in a paraxial domain.

In such a surface examining method, because the image pickup part is inclined in a direction in which a fading portion (vagueness) is cleared from the image, the fading portion can be corrected. As a result, the method enables highly reliable examination.

The illuminating light may be directed to the object to be measured in a direction which is different from that of an extended line of the optical axis of the object-side telecentric optical system or the image-object-side telecentric optical system.

In such a surface examining method, because the object to be measured is illuminated from a direction which is different from that of an extended line of the optical axis of the object-side telecentric optical system or the image-object-side telecentric optical system, a half mirror is not required. As a result, it is possible to have no effect of a ghost caused by the half mirror on the image and to prevent reduction of the amount of light which might be caused by using the half mirror. Further, because the half mirror is not required, the cost of the surface examining apparatus can be decreased.

In accordance with another aspect of the present invention, the surface examining method for examining a surface condition of an object to be measured by observing a light reflected from the object through an object-side telecentric optical system, comprises the steps of; arranging the object-side telecentric optical system so that an optical axis thereof is inclined with respect to a direction normal to the object to be measured, forming an air image corresponding to a surface to be examined, of the object to be measured by using the object-side telecentric optical system, and observing the air image.

In such a surface examining method, the air image is observed by a predetermined optical system. In the case of a construction of the optical system, preferably, optical parts are suitably chosen and arranged to eliminate the effect of far and near distances from the object on the image to be observed. As a result, the correction of the unbalanced state of the image, which might be caused by the far and near distances from the object is not required in the step of an image processing.

In accordance with another aspect of the present invention, the surface examining method for examining a surface condition of an object to be measured by observing a light reflected from the object through an object-side telecentric optical system, comprises the steps of; arranging the object-side telecentric optical system so that an optical axis thereof is inclined with respect to a direction normal to the object to be measured, forming an image corresponding to a surface to be examined, of the object to be measured on a ground glass by using the object-side telecentric optical system, and observing the image.

In such a surface examining method, the formed image on the ground glass is observed through a predetermined optical system. In the case of a construction of the optical system, preferably, optical parts are suitably chosen and arranged to eliminate the effect of far and near distances from the object on the image to be observed. As a result, the correction of the unbalanced state of the image, which might be caused by the far and near distances from the object is not required in the step of an image processing.

When the surface of the object to be measured is examined, the object to be measured may be rotated in parallel with the surface to be examined, that is, around the normal of the surface to be examined, of the object to be measured.

In accordance with another aspect of the present invention, in the surface examining apparatus for examining a surface condition of an object to be measured, by observing a light reflected from the object through an object-side telecentric optical system or an image-object-side telecentric optical system, the object-side telecentric optical system or the image-object-side telecentric optical system is arranged so that an optical axis thereof is inclined at a predetermined angle with respect to a direction normal to the object to be measured.

In such a surface examining apparatus, because the object-side telecentric optical system or the image-object-side telecentric optical system is arranged so that an optical axis thereof is inclined with respect to a direction normal to the object to be measured, it is possible to examine a wide region on the surface to be examined and to reduce the size of the apparatus for examining, in a direction normal to the surface to be examined.

It is preferable that the surface examining apparatus further comprises an image pickup part at which an image of the light issued from the object-side telecentric optical system or the image-object-side telecentric optical system is formed, wherein the image pickup part is inclined so as to coincide with an image plane in a paraxial domain.

In such a surface examining apparatus, because the image pickup part is inclined in a direction in which a fading portion (vagueness) is cleared from the image, the fading portion can be corrected. As a result, the apparatus enables highly reliable examination.

In accordance with another aspect of the present invention, in the surface examining apparatus for examining a surface condition of an object to be measured, by observing a light reflected from the object through an object-side telecentric optical system or an image-object-side telecentric optical system, the object-side telecentric optical system or the image-object-side telecentric optical system is arranged so that an optical axis thereof can be inclined at a predetermined angle with respect to a direction normal to the object to be measured.

In such a surface examining apparatus, because the object-side telecentric optical system or the image-object-side telecentric optical system is constructed so that an optical axis thereof can be inclined at a predetermined angle with respect to a direction normal to the object to be measured in case of necessity, it is possible to examine a wide region on the surface to be examined. On the other hand, it is also convenient that the object-side telecentric optical system or the image-object-side telecentric optical system is arranged so that the optical axis can coincide with the direction normal to the object to be measured.

It is preferable that the surface examining apparatus comprises an image pickup part at which an image of the light issued from the object-side telecentric optical system or the image-object side telecentric optical system is formed, wherein the image pickup part can be inclined so as to coincide with an image plane in a paraxial domain.

In such a surface examining apparatus, because the image pickup part can be inclined in a direction in which a fading portion is cleared from the image in case of necessity, the fading portion can be corrected. As a result, the apparatus enables highly reliable examination.

The surface examining apparatus may comprise a ground glass instead of the image pickup part.

In such a surface examining apparatus, because an air image is formed and observed, the unbalanced state of the image, which might be caused by the far and near distances from the object can be cleared from the image to be observed optically without an image processing. Further, because the image is formed on the ground glass, it is easy to focus the image formed on the ground glass.

The surface examining apparatus may further comprise a mirror for illuminating the object to be measured in a direction which is different from that of an extended line of the optical axis of the optical system. Further, the number of the mirrors may be not less than two, wherein the mirrors are arranged to illuminate the object to be measured in a direction which is different in directions from that of one another.

The surface examining apparatus may further comprise a rotating device for rotating the object to be measured in parallel with the surface to be examined, of the object to be measured.

BEST MODE OF THE INVENTION

FIRST EMBODIMENT

Figure 1:
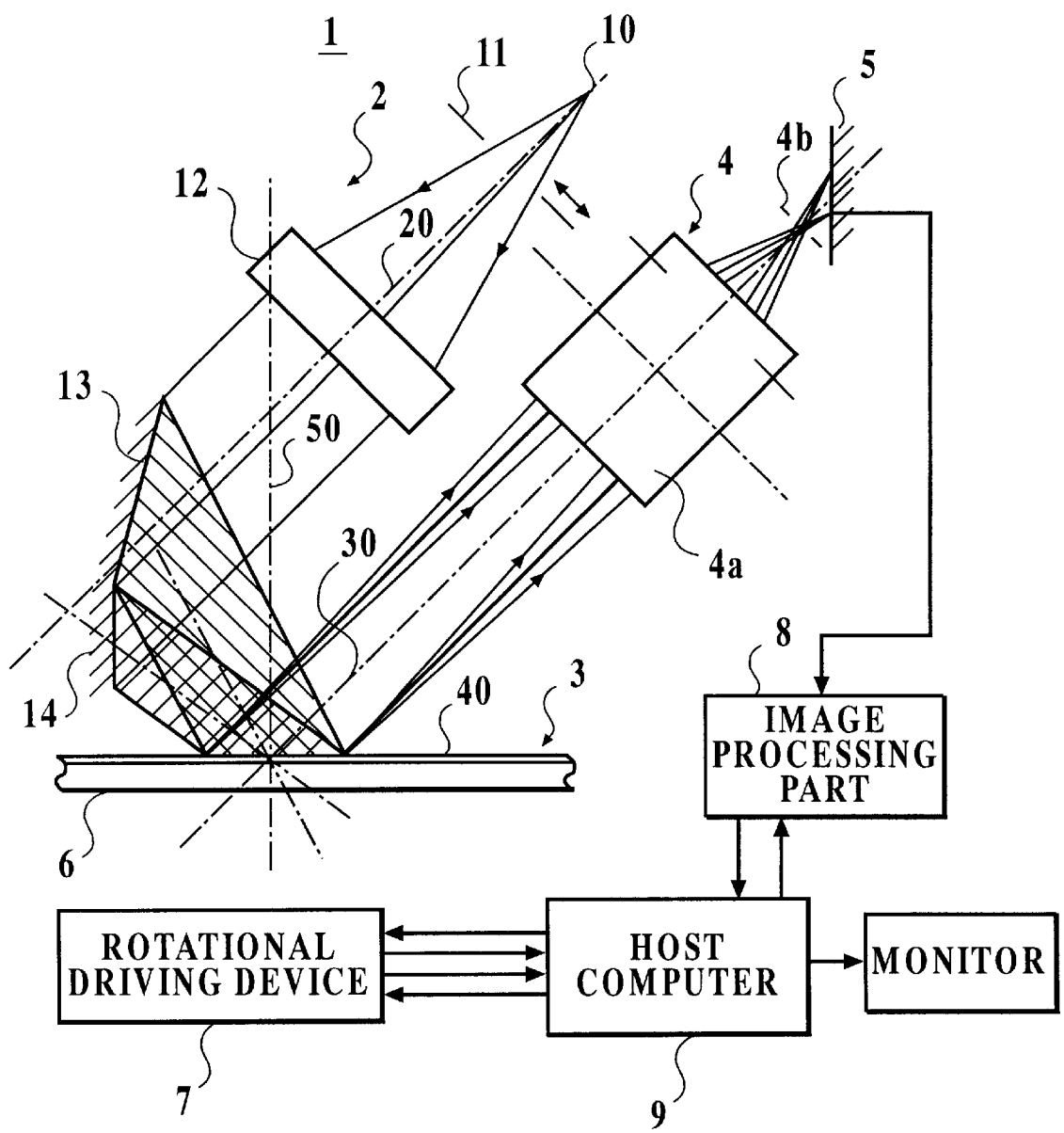
FIG. 1 is a view of a construction of a surface examining apparatus according to the first embodiment of the present invention.

FIG. 1 shows a construction of a surface examining apparatus according to the first embodiment of the present invention. As shown in FIG. 1, the surface examining apparatus 1 is constructed so that a light illumination member 2 illuminates a semiconductor wafer 3 as an object to be measured, with a substantially parallel light formed thereby and then an image of the light reflected from the semiconductor wafer 3 is formed at an image pickup part 5 by an object-side telecentric optical system 4. A table 6 for supporting the semiconductor wafer 3 is rotated by a rotational driving device 7. The image pickup part 5 is electrically connected to an image processing part 8. After an amplification of the image signal outputted from the image pickup part 5, the image processing part 8 converts it into a digital image signal and outputs the digital image signal to a host computer 9. The host computer 9 corrects the digital image signal outputted from the image processing part 8 and then observes an irregular condition of a surface of the semiconductor wafer 3 and detects ID (Identification) number previously designated to the surface to be examined, of the semiconductor wafer 3. The reason why the host computer corrects the digital image signal will be explained below.

The above-mentioned light illumination member 2 of the surface examining apparatus 1 comprises a light source 10, a variable stop 11, a collimating lens 12 and two mirrors 13 and 14. On the other hand, the object-side telecentric optical system 4 comprises a telecentric lens 4a and a stop 4b located at a position of stop.

The light source 10 comprises LEDs arranged at a plurality of points. Needless to say, the light source 10 is not limited to the LEDs arranged at a plurality of points. For example, the light source 10 may be a halogen lamp, a light source having bundled optical fibers or other light sources. In the case of using a halogen lamp, the light source 10 preferably has a construction to dispose a stop at a front-side focal point (an object focal point) of the collimating lens 12 or at a neighboring position thereof in order to use the light source as a substantial point light source. The variable stop 11 limits a light issued from the light source 10, to the certain amount of light. The variable stop 11 can vary an aperture diameter thereof and can be moved in a direction normal to an optical axis 20 by a driving device which is not shown in the figure. The collimating lens 12 converts a light issued from the light source 10 into a parallel light. Two mirrors 13 and 14 for changing a direction of a light passing through the collimating lens 12 are arranged so that the angle of the mirror 13 with respect to the optical axis 20 is different from that of the mirror 14. The mirror illuminated with the parallel light passing through the collimating lens 12 is chosen between two mirrors 13 and 14 by a movement of the variable stop 11. An optical axis 30 of the object-side telecentric optical system 4 is inclined with respect to a normal line 50 of a surface 40 to be examined, of the semiconductor wafer 3. The stop 4b limits a light issued from the telecentric lens 4a, to the certain amount of light. The image pickup part 5 is inclined with respect to the optical axis 30 so that a surface of the image pickup part, for forming an image coincides with an image plane of paraxial ray reflected from the surface 40 to be examined, of the semiconductor wafer 3. Because the image of the paraxial ray is in focus at the all points of the image plane, the fading potions are cleared by inclining the image pickup part 5 with respect to the optical axis 30.

Next, the reason why the digital image signal is corrected by the host computer 9 will be explained below.

Figure 2:
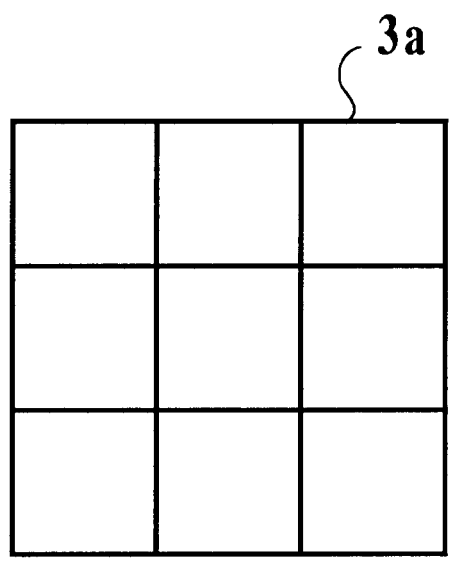
FIG. 2 is a view showing a virtual irregular pattern formed on the semiconductor wafer.
Figure 3:
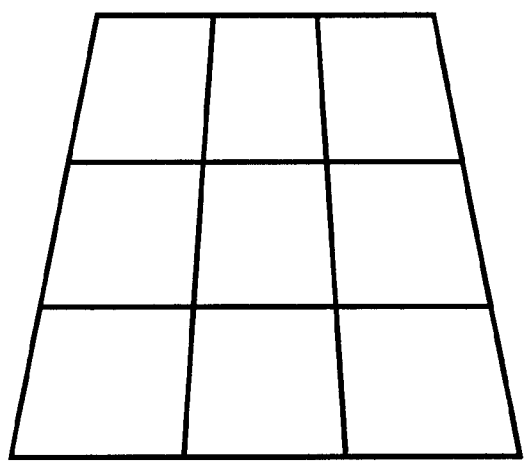
FIG. 3 is a view showing an image formed at the image pickup part.

When we assume that an irregular pattern 3a having a lattice shape shown in FIG. 2 is formed on the semiconductor wafer 3, an effect of the difference between the far and near distances from the portion of the pattern occurs on the image of the irregular pattern 3a, which is formed at the image pickup part 5, and in the digital image signal which corresponds to the image, as shown in FIG. 3. In order to correct the state including the effect caused by the far and near distances, it is necessary that the digital image signal is corrected so as to form the image and the digital image signal, as shown in FIG. 2. Then, the digital image signal is inputted to the host computer 9 to correct the unbalanced state of the image caused by the effect of the difference between the far and near distances.

As described above, when the digital image signal is corrected, the state of the surface of the semiconductor wafer 3 can be examined precisely.

The surface examining method for examining the semiconductor wafer 3, which is carried out by the surface examining apparatus 1 will be explained.

The semiconductor wafer 3 is mounted on the table 6. A light is directed to the semiconductor wafer 3 from the light source 10. In this case, the variable stop 11 is fixed at a predetermined position, for example, a position at which the variable stop 11 is fixed so that only the mirror 13 is illuminated with the light issued from the collimating lens 12. After the light emitted from the light source 10 passes through the collimating lens 12, the light is reflected from the mirror 13, and then is directed to the semiconductor wafer 3. The image of the light reflected from the semiconductor wafer 3 is formed at the image pickup part 5 through the object-side telecentric optical system 4. After the image signal outputted from the image pickup part 5 is amplified by the image processing part 8, the image signal is converted into the digital image signal and then the digital image signal is outputted to the host computer 9. The digital image signal is corrected by the host computer 9.

Next, the table 6 is rotated each 90 degrees, and the above-mentioned process is carried out every rotation of the table 6. The images are synthesized on the basis of the digital image signals corrected by the host computer 9.

Subsequently, only the mirror 14 is illuminated with the light issued from the collimating lens 12 by a movement of the variable stop 11, and then the above-mentioned process is carried out. The reason why one mirror is switched to the other between the mirrors 13 and 14, is that there is an illuminating angle at which the irregularity can be easily detected according to the size and the shape, thereof. Thereby, the status of the surface of the semiconductor wafer 3 can be examined more precisely.

According to the surface examining apparatus 1, because the object-side telecentric optical system 4 is arranged so that an optical axis 30 is inclined with respect to a direction normal to the semiconductor wafer 3, it is possible to examine a wide region on the surface 40 to be examined and to reduce the size of the apparatus for examining, in a direction normal to the surface 40 to be examined. Further, in such a surface examining apparatus 1, because the shape and the height, of a bump (an electrode) of a semiconductor integrated circuit formed on the semiconductor wafer 3 can be precisely detected, the apparatus enables an effective examination of a defective bump or the like.

Because the object-side telecentric optical system 4 is used, the aberration is smaller against the change of the magnification as compared with a normal optical system. As a result, although the optical axis 30 is inclined, it is possible to carry out the precise examination. Further, because the object 3 to be measured is illuminated from a direction which is different from that of an extended line of the optical axis 30 of the object-side telecentric optical system 4, a half mirror is not required. As a result, it is possible to have no effect of a ghost caused by the half mirror on the image and to prevent reduction of the amount of light, which might be caused by using the half mirror. Further, because the half mirror is not required, the cost of the surface examining apparatus 1 can be decreased.

SECOND EMBODIMENT

Figure 4:
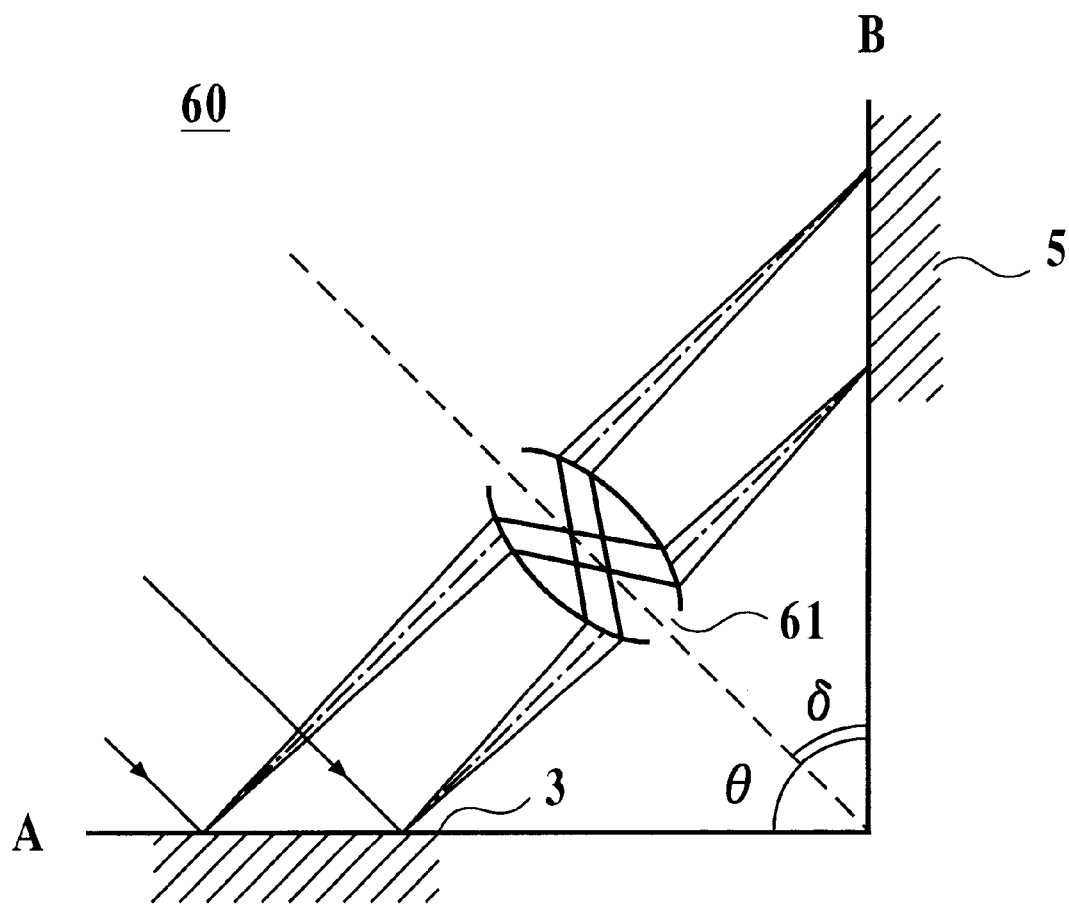
FIG. 4 is a view of a construction of a surface examining apparatus according to the second embodiment of the present invention.

FIG. 4 shows a construction of a surface examining apparatus according to the second embodiment of the present invention. As shown in FIG. 4, a difference between the surface examining apparatus 60 and the surface examining apparatus 1 according to the first embodiment is that the surface examining apparatus 60 has an image-object-side telecentric optical system (a both sides telecentric optical system) 61 instead of the object-side telecentric optical system 4 of the surface examining apparatus 1 according to the first embodiment. In such a surface examining apparatus 60 according to the second embodiment, the inclinations of the surfaces A and B and that of the image-object-side telecentric optical system 60 are set by suitably giving the values of θ and δ so that an object and an image are conjugate in a paraxial domain. In the other points, the construction of the surface examining apparatus 60 is approximately similar to that of the surface examining apparatus 1 according to the first embodiment. The members constituting the surface apparatus 60, which corresponds to those of the surface examining apparatus 1 according to the first embodiment are denoted by the same references as those of the surface examining apparatus 1, and the explanations thereof are omitted.

According to the surface examining apparatus 60, because the image pickup part 5 coincides with the image plane in a paraxial domain, the fading portions can be cleared from the image. Further, because the principal rays are also parallel to the optical axis of the image-object-side telecentric optical system in the image space, the unbalanced state of the image formed on the surface B, which is caused by the effect of the difference between the far and near distances from the surface to be measured, does not occur. As a result, the image processing is not required.

Although the present invention has been explained according to the embodiments, it should also be understood that the present invention is not limited to the embodiments and that various changes and modifications may be made to the invention without departing from the gist thereof.

For example, in the first embodiment, the image pickup part 5 is provided behind the object-side telecentric optical system 4, however, a ground glass may be provided instead of it, or the air image may be formed without a ground glass.

In the first embodiment, the object-side telecentric optical system 4 and the image pickup part 5 are fixedly provided, however, the surface examining apparatus may have a construction in which the inclination angles of the object-side telecentric optical system 4 and the image pickup part 5 can be changed freely. In this case, it is preferable that when the inclination of the object-side telecentric optical system 4 is changed, the angle of the image pickup part 5 can be changed suitably so as to work with the object-side telecentric optical system 4. In this case, the image-object-side telecentric optical system 61 may be used instead of the object-side telecentric optical system 4.

Further, in the embodiments, a semiconductor wafer is illustrated as an object to be measured, however, all of the objects having an approximately flat surface may also be used. In this case, an approximately flat surface is referred to a flat surface as a whole, which has an irregularity microscopically.

The entire disclosure of Japanese Patent Application No. Tokugan-Hei 9-175999 filed on Jul. 1, 1997 including specification, claims drawings and summary are incorporated herein by reference in its entirety.

Industrial Applicability

Typical effects according to the present invention will be explained as follows. In the surface examining apparatus for examining a surface of an object to be measured, by observing a light reflected from the object through an object-side telecentric optical system or an image-object-side telecentric optical system, because the object-side telecentric optical system or the image-object-side telecentric optical system is constructed so that an optical axis thereof is inclined with respect to a direction normal to the object to be measured and the light reflected from the object to be measured is observed, it is possible to examine a wide region on the surface to be examined and to reduce the size of the apparatus for examining, in a direction normal to the surface to be examined.

What is claimed is:

1. A surface examining apparatus for examining a surface condition of an object to be measured, by observing a light reflected from the object through an object-side telecentric optical system or an image-object-side telecentric optical system, wherein the object-side telecentric optical system or the image-object-side telecentric optical system is arranged so that an optical axis thereof is inclined at a predetermined angle with respect to a direction normal to the object to be measured, and a mirror for illuminating the object to be measured in a direction which is different from that of an extended line of the optical axis of the object-side telecentric optical system or the image-object-side telecentric optical system, wherein the number of the mirror is not less than two, and the mirror are arranged to illuminate the object to be measured in a direction which is different from that of one another.

2. A surface examining apparatus as claimed in claim 1, further comprising an image pickup part at which an image of the light issued from the object-side telecentric optical system or the image-object-side telecentric optical system is formed, wherein the image pickup part is included so as to coincide with an image plane in a paraxial domain.

3. A surface examining apparatus as claimed in claim 1, further comprising a ground glass instead of the image pickup part.

4. A surface examining apparatus as claimed in claim 1, further comprising a rotating device for rotating the object to be measured parallel with the surface to be examined, of the object.

* * * * *